(12) United States Patent
Li

(10) Patent No.: US 6,237,355 B1
(45) Date of Patent: May 29, 2001

(54) PRECOOLED CRYOGENIC ABLATION SYSTEM

(75) Inventor: Hong Li, San Diego, CA (US)

(73) Assignee: CryoGen, Inc., San Diego, CA (US)

( * ) Notice: Subject to any disclaimer, the term of this patent is extended or adjusted under 35 U.S.C. 154(b) by 0 days.

(21) Appl. No.: 09/344,423

(22) Filed: Jun. 25, 1999

(51) Int. Cl.$^7$ .............. F25D 3/00; F25B 9/00; F25B 7/00

(52) U.S. Cl. .............. 62/293; 62/6; 62/114; 62/335

(58) Field of Search .............. 62/6, 293, 335, 62/114; 606/20, 22, 25

(56) References Cited

U.S. PATENT DOCUMENTS

| | | | |
|---|---|---|---|
| 2,991,633 | 7/1961 | Simon | 62/514 |
| 3,048,021 | 8/1962 | Coles et al. | 62/36 |
| 3,401,533 | 9/1968 | Maybury | 62/54 |
| 3,415,078 | * 12/1968 | Liston | 62/514 |
| 3,431,750 | 3/1969 | LeFranc | 62/514 |
| 3,696,813 | 10/1972 | Wallach | 128/303.1 |
| 4,829,785 | * 5/1989 | Hersey | 62/467 |
| 4,840,043 | 6/1989 | Sakitani et al. | 62/51.2 |
| 4,875,346 | 10/1989 | Jones et al. | 62/467 |
| 4,951,471 | 8/1990 | Sakitani et al. | 62/51.2 |
| 4,990,412 | 2/1991 | Hersey | 429/8 |
| 5,063,747 | 11/1991 | Jones et al. | 62/461 |
| 5,157,938 | 10/1992 | Bard et al. | 62/335 |
| 5,207,674 | * 5/1993 | Hamilton | 606/20 |
| 5,275,595 | 1/1994 | Dobak, III | 606/23 |
| 5,595,065 | 1/1997 | Boiarski et al. | 62/222 |
| 5,617,739 | 4/1997 | Little | 62/619 |
| 5,724,832 | 3/1998 | Little et al. | 62/613 |
| 5,758,505 | * 6/1998 | Dobak et al. | 62/6 |
| 5,759,182 | 6/1998 | Varney et al. | 606/21 |
| 5,807,391 | 9/1998 | Wijkamp | 606/23 |

FOREIGN PATENT DOCUMENTS

| | | |
|---|---|---|
| WO95/13025 | * 5/1995 | (WO) . |
| WO 99/15093 | 4/1999 | (WO) . |

OTHER PUBLICATIONS

Chang, Z.; *Development of a High Performance Multiprobe Cryosurgical Device*; 09/1994; Biomedical Instrumentation and Technology; pp. 383–390.

Little, W.; *Advances in Joule–Thomson Cooling*; pp. 1–10; place and date of publication unknown.

Little, W.; *Microminiature Refrigeration*; 06/1983; Rev. Sci. Instrum. 55(5); pp. 661–680.

Little, W.; *Microminiature Refrigerators for Joule–Thomson Cooling of Electronic Chips and Devices*; 1990; Advances in Cryogenic Engineering vol. 35; pp. 1325–1333.

* cited by examiner

Primary Examiner—William Doerrler
(74) Attorney, Agent, or Firm—Gerald W. Spinks

(57) ABSTRACT

A method and apparatus for using a secondary refrigerant to precool and liquefy a primary refrigerant, then vaporizing and expanding the primary refrigerant to cool a cold tip of a cryosurgical instrument for ablation of biological tissue, such as cardiovascular tissue, in particular endocardiac tissue and tissue inside a cardiac blood vessel. The secondary refrigerant has a critical temperature above the critical temperature of the primary refrigerant, and a cooling temperature below the critical temperature of the primary refrigerant, thereby facilitating the use of the precooling step to provide liquid primary refrigerant in an operating room environment in which the primary refrigerant could not otherwise be provided in the liquid phase.

1 Claim, 1 Drawing Sheet

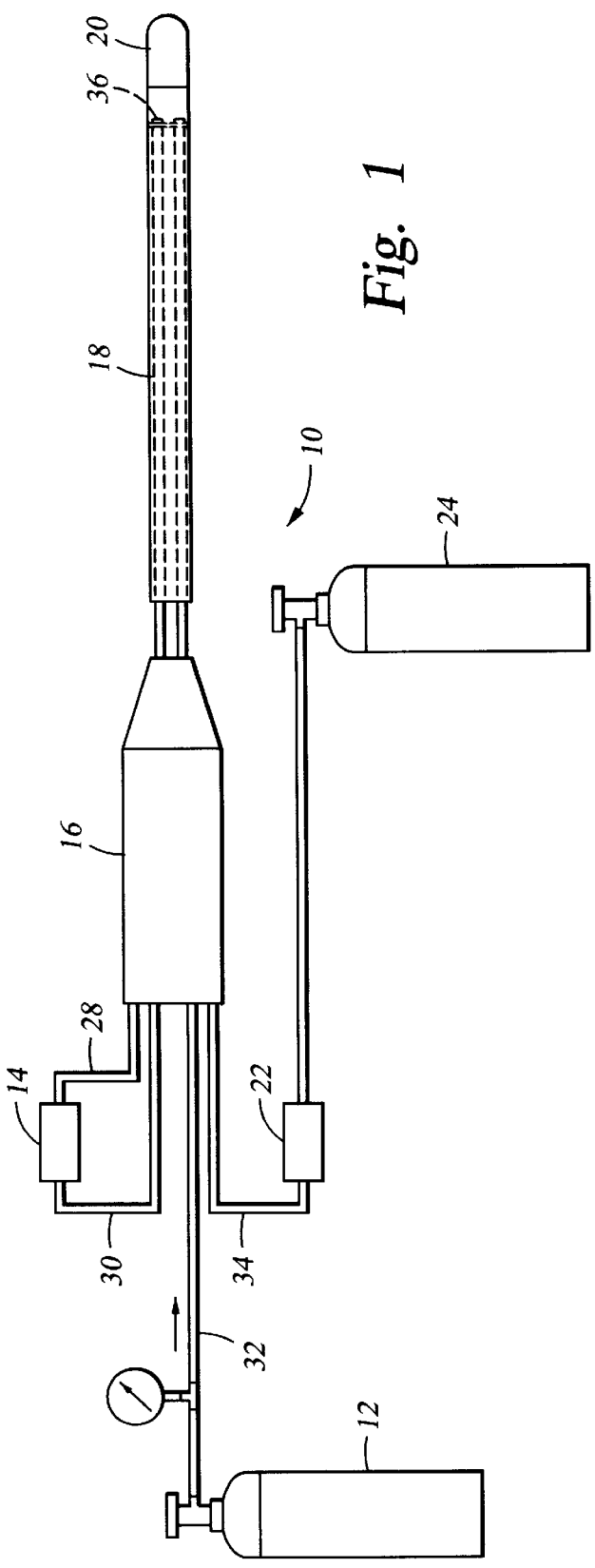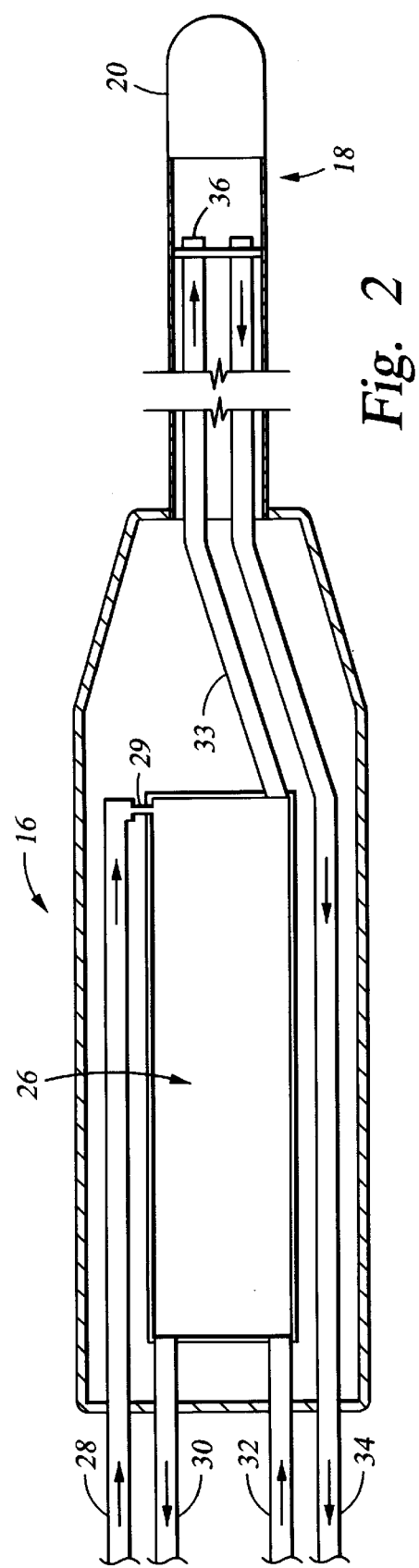

PRECOOLED CRYOGENIC ABLATION SYSTEM

CROSS REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention is in the field of cooling biological tissues to very low temperatures, for treatment of medical conditions, as in cryosurgery.

2. Background Information

It is desirable to be able to selectively cool miniature discrete portions of biological tissue to very low temperatures in the performance of cryosurgery, without substantially cooling adjacent tissues of the organ. Cryosurgery has become an important procedure in medical, dental, and veterinary fields. Particular success has been experienced in the specialties of gynecology and dermatology. Other specialties, such as neurosurgery and urology, could also benefit from the implementation of cryosurgical techniques, but this has only occurred in a limited way. Unfortunately, currently known cryosurgical instruments have several limitations which make their use difficult or impossible in some such fields. Specifically, known systems can not achieve the necessary temperature and cooling power to optimally perform cryosurgical ablation, such as in cardiac ablation to correct arrhythmia.

In the performance of cryosurgery, it is typical to use a cryosurgical application system designed to suitably freeze the target tissue, thereby destroying diseased or degenerated cells in the tissue. The abnormal cells to be destroyed are often surrounded by healthy tissue which must be left uninjured. The particular probe, catheter, or other applicator used in a given application is therefore designed with the optimum shape, size, and flexibility or rigidity for the application, to achieve this selective freezing of tissue. Where a probe or catheter is used, the remainder of the refrigeration system must be designed to provide adequate cooling, which involves lowering the operative portion of the probe to a desired temperature, and having sufficient power or capacity to maintain the desired temperature for a given heat load. The entire system must be designed to place the operative portion of the probe or catheter at the location of the tissue to be frozen, without having any undesirable effect on other organs or systems.

It is an object of the present invention to provide a method and apparatus for precooling a primary loop high pressure refrigerant to a point below its critical temperature, to liquefy the primary refrigerant, with a secondary loop refrigeration cycle. This allows the use of a liquid primary refrigerant having a critical temperature below the operating room temperature, in order to achieve the lower temperature possible with such a primary refrigerant.

BRIEF SUMMARY OF THE INVENTION

The present invention comprises a miniature refrigeration system, including a method for operating the system, including precooling of the primary high pressure refrigerant below its critical temperature, to liquefy the primary refrigerant, with a secondary refrigeration cycle using a second refrigerant with a higher critical temperature, to maximize the available cooling power of the primary refrigerant, and to achieve the lowest possible temperature.

The cooling power is an important design parameter of a cryosurgical instrument. With greater cooling power, more rapid temperature decreases occur, and lower temperatures can be maintained at the probe tip during freezing. This ultimately leads to greater tissue destruction. The power of a J-T cryosurgical device is a function of the enthalpy difference of the primary refrigerant and the mass flow rate. Pre-cooling a refrigerant below its critical temperature and liquefying the refrigerant will increase the enthalpy difference available for cooling power.

An example of a suitable primary refrigerant is SUVA-95, a mixture of R-23 and R-116 refrigerants made by DuPont Fluoroproducts, of Wilmington, Del. SUVA-95 has a critical temperature of 287K, with cooling capacity at temperatures as low as 185K at one atmosphere. An example of a suitable secondary refrigerant is AZ-20, an R-410a refrigerant made by Allied Signal of Morristown, N.J. AZ-20 has a critical temperature of 345K, with cooling capacity at temperatures as low as 220K at one atmosphere.

The high pressure primary refrigerant is fed as a gas into a high pressure passageway within a primary-to-secondary heat exchanger. The primary-to-secondary heat exchanger can be a coiled tube heat exchanger or a finned tube heat exchanger. The liquid secondary refrigerant is vaporized and expanded into a low pressure passageway in the primary-to-secondary heat exchanger. Heat exchange between the low pressure secondary refrigerant vapor and the high pressure primary refrigerant cools and liquefies the high pressure refrigerant. The liquid high pressure primary refrigerant is then vaporized and expanded at the cooling tip of a cryosurgical catheter to provide the cooling power necessary for effective ablation of tissue. The method and apparatus of the present invention can be used equally well in a rigid hand held cryoprobe, or in a catheter.

The primary-to-secondary heat exchanger is part of the secondary refrigeration system, which can have a secondary compressor and a secondary expansion element, in addition to the primary-to-secondary heat exchanger. The liquid high pressure secondary refrigerant, having a higher critical temperature than the primary refrigerant, can be at a temperature which is relatively higher than the critical temperature of the primary refrigerant. However, the vaporized and expanded low pressure secondary refrigerant is at a temperature which is low enough to cool the primary refrigerant below its critical temperature. Since the secondary refrigerant has a critical temperature above normal operating room temperature, it can easily be provided in the liquid state in an operating room environment, whereas the primary refrigerant, which has a critical temperature significantly below normal operating room temperature, can not.

The liquid high pressure primary refrigerant is conducted from the heat exchanger to the inlet of a primary Joule-Thomson expansion element located in the cold tip of the probe or catheter, where the primary refrigerant is vaporized and expanded to a lower pressure and a lower temperature.

The primary refrigerant exiting the primary Joule-Thomson expansion element is exposed to the inner surface of a heat transfer element at the cold tip. The vaporized and expanded primary refrigerant cools the heat transfer element to a lower temperature and then returns through the low pressure return passageway of the catheter or probe.

The novel features of this invention, as well as the invention itself, will be best understood from the attached drawings, taken along with the following description, in which similar reference characters refer to similar parts, and in which:

BRIEF DESCRIPTION OF THE SEVERAL VIEWS OF THE DRAWINGS

FIG. 1 is a schematic view of the preferred embodiment of the apparatus of the present invention; and FIG. 2 is a schematic section view of the primary-to-secondary heat exchanger used in the apparatus shown in FIG. 1.

DETAILED DESCRIPTION OF THE INVENTION

The present invention lies in the appropriate use of a secondary evaporative refrigeration system to precool and liquefy the primary high pressure refrigerant, before passage of the primary refrigerant through a primary Joule-Thomson expansion element. This is intended to enable the generation of a sufficiently low temperature, and to maximize the available cooling power, at the cold tip of a cryosurgical probe or catheter.

Pre-cooling the primary refrigerant to an at least partially liquid state, prior to feeding it to the primary expansion element, is the focus of the present invention. This pre-cooling can be done prior to introducing the primary refrigerant into the catheter, by the use of a heat exchanger in a cooling console. Alternatively, pre-cooling can be provided nearer to the treatment area, such as in the handle of a cryoprobe, or at the proximal end of a catheter.

An important parameter in the design of a cryosurgical device is the cooling power which the refrigeration system can develop. The cooling power determines the rate of cooling in degrees per second, and the temperature which can be maintained at the probe tip during freezing of the tissue. The rate of freezing is important in achieving cell death, since more rapid freezing results in better formation of intracellular ice crystals, resulting in cell lysis. The rate of freezing also determines the length of time required to perform a given procedure on the patient. The quicker the procedure, the less traumatic the procedure is to the patient.

The temperature which can be maintained at the probe cold tip determines the size of the ice ball formed in the surrounding tissue. This, of course, determines the total volume of tissue destroyed at each location, and the speed with which the procedure can be completed.

In Joule-Thomson cryosurgical devices, high pressure fluid expands across a restriction of some kind, such as a small orifice, or a restricted tube. The sudden drop in pressure results in a corresponding drop in temperature. The cooling power of the device is the product of the mass flow rate of the cryogen and the enthalpy difference at the different pressures and temperatures. The flow rate is a function of orifice size and the temperature and pressure of the cryogen. For a given orifice size, under non-choking conditions, the density of the cryogen is higher at higher pressures and lower temperatures, resulting in a higher mass flow rate. The maximum flow rate is found at the point where the cryogen is a liquid. The enthalpy difference is also a function of the pressure and temperature. For a given temperature and a given pressure, the maximum enthalpy difference between two conditions occurs at the liquefaction point of the cryogen. Incorporating a pre-cooling heat exchanger into the refrigeration system, to promote liquefaction of the high pressure primary cryogen, increases the power of the system.

If the primary refrigerant is in the gaseous state upon startup of the refrigeration system, the early flow rate is very low, and the power is very low. Therefore, the initial cool down is very slow at overcoming the low flow rate. Further, the cold tip is typically placed within the patient, and in contact with the target tissue, before commencement of cooldown, placing a significant heat load on the tip. This means that cooldown can be unacceptably slow, and in some cases, it may not occur at all.

In order to maximize the performance of the present cryosurgical system, and to eliminate the problems normally associated with slow cooldown rates and low cooling power, an independent secondary evaporative refrigeration system is incorporated. The primary system uses a refrigerant such as freon, or SUVA-95, to achieve the desired temperature and capacity at the cold tip. However, the critical temperature of such a refrigerant is below the temperature normally found in the operating room environment, so provision of the primary refrigerant in the liquid state requires precooling. The secondary system uses a refrigerant such as AZ-20, to pre-cool and liquefy the primary refrigerant prior to flow of the primary refrigerant to the cold tip. The secondary system accomplishes this pre-cooling through a primary-to-secondary heat exchanger. This pre-cooling causes the initial flow rate and the cooling power of the system to be higher, making the initial cooldown rate much faster.

As shown in FIG. 1, the apparatus 10 of the present invention includes a source of gaseous high pressure primary refrigerant 12, a source of liquid high pressure secondary refrigerant 14, a primary-to-secondary heat exchange unit 16, and a probe or catheter 18 with a cold tip 20. The gaseous primary refrigerant source 12 can incorporate a pressure bottle as schematically shown, with the primary loop being an open loop, or the source 12 can incorporate a compressor, with the primary loop being a closed loop, as will be explained below. The primary refrigerant is one which, in order to deliver the desired temperature and cooling capacity at the cold tip 20, necessarily has a critical temperature below the temperature of the operating room environment. The purpose of the present invention is to cool that gaseous pimary refrigerant below its critical temperature and convert it to a liquid refrigerant, in order to achieve the desired temperature and cooling capacity. A flexible coaxial catheter 18 can be constructed with an outer tube made of pebax, and an inner tube made of polyimide.

Gaseous high pressure primary refrigerant flows from the primary refrigerant source 12 via a conduit 32 into the heat exchange unit 16. After heat exchange and liquefaction, liquid primary refrigerant, at a temperature below the temperature of the operating room environment, flows from the heat exchange unit 16 into the catheter or probe 18. Near the distal tip of the catheter 18, the liquid primary refrigerant is vaporized and expanded at an expansion element shown schematically as an orifice 36. This lowers the temperature of the primary refrigerant to the desired temperature, enabling the refrigerant to cool the cold tip 20 to the selected temperature for tissue ablation. Gaseous primary refrigerant returning from the cold tip 20 exits the heat exhange unit 16 via a conduit 34. Where the primary refrigerant source 12 incorporates a pressure bottle, the primary loop can be operated as an open loop, and the gaseous primary refrigerant conduit 34 can be collected by a compressor 22 to vent to atmosphere or to a collector 24. Alternatively, the primary loop can be operated as a closed loop, and the gaseous primary refrigerant conduit 32 can be routed (not shown) from the outlet of the compressor 22, as is well know in the art.

The liquid secondary refrigerant source 14 can incorporate a compressor unit as schematically shown, or it can incorporate a pressure bottle. If required to generate the necessary pressure for liquefaction of the secondary refrigerant, a compressor can be used to raise the pressure of the effluent from a pressure bottle. The secondary refrigerant source 14 can also include a condenser, as is well known in the art, for liquefying the secondary refrigerant, if required. The secondary refrigerant must be one which has a critical temperature above the temperature of the operating room environment, so that the secondary refrigerant can be conducted in liquid form to the primary-to-secondary heat exchange unit 16. This enables the use of the phase-change enthalpy difference in the secondary refrigerant to provide the necessary cooling to take the primary refrigerant below its critical temperature in the heat exchange unit 16.

Liquid high pressure secondary refrigerant, at a temperature above the temperature of the operating room environment, flows from the secondary refrigerant source 14 via a conduit 28 into the heat exchange unit 16. After vaporization and heat exchange, gaseous secondary refrigerant flows from the heat exchange unit 16 via a conduit 30. Where the secondary refrigerant source 14 incorporates a pressure bottle, the secondary loop can be operated as an open loop, and the gaseous secondary refrigerant conduit 30 can vent to atmosphere or to a collector (not shown) as is well known in the art. Alternatively, the secondary loop can be operated as a closed loop, and the gaseous secondary refrigerant conduit 30 can be routed to the inlet of a compressor in the secondary refrigerant source 14, as shown.

As shown schematically in FIG. 2, liquid high pressure secondary refrigerant enters the heat exchange unit 16 via a supply conduit 28 and is vaporized and expanded via a secondary expansion element shown as a capillary tube 29. The vaporized and expanded secondary refrigerant, at a temperature below the critical temperature of the primary refrigerant, then flows through a secondary refrigerant flow path in a primary-to-secondary heat exchanger 26 and exits the heat exchange unit 16 via a return conduit 30.

Gaseous high pressure primary refrigerant enters the heat exchange unit 16 via a supply conduit 32 and flows through a primary refrigerant flow path in the heat exchanger 26. Since the temperature of the secondary refrigerant flowing through the heat exchanger 26 is significantly below the critical temperature of the primary refrigerant, the primary refrigerant is liquefied in the heat exchanger 26. Liquid primary refrigerant then exits the heat exchanger via a conduit 33 and flows through the catheter 18 to a primary expansion element, shown schematically as an orifice 36, near the cold tip 20. The primary expansion element 36 vaporizes and expands the primary refrigerant to the selected temperature for cooling the cold tip 20 to the desired temperature for ablation of tissue. The vaporized and expanded primary refrigerant returning from the cold tip 20 then flows back through the catheter 18, through the heat exchange unit 16, and exits the heat exchange unit 16 via a return conduit 34.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

I claim:

1. A cryosurgical instrument for ablation of endocardiac tissue, comprising:

a source of a gaseous primary refrigerant said source providing said primary refrigerant at a temperature above the critical temperature of said primary refrigerant;

a source of a liquid secondary refrigerant, said secondary refrigerant having a critical temperature higher than said critical temperature of said primary refrigerant;

a secondary expansion element connected to receive said liquid secondary refrigerant, said secondary expansion element being constructed to vaporize and expand said secondary refrigerant to a temperature below said critical temperature of said primary refrigerant;

a primary-to-secondary heat exchanger having a primary refrigerant flow path connected to receive said gaseous primary refrigerant, and a secondary refrigerant flow path connected to receive said vaporized and expanded secondary refrigerant from said secondary expansion element, said heat exchanger being constructed to cool and liquefy said primary refrigerant;

a primary expansion element connected to receive said liquid primary refrigerant from said heat exchanger, said primary expansion element being constructed to vaporize and expand said primary refrigerant to a selected cryogenic temperature; and a cryoablation heat transfer element connected to receive said vaporized and expanded primary refrigerant;

wherein said primary refrigerant comprises SUVA-95, and said secondary refrigerant comprises AZ-20.

* * * * *